US009079182B2

(12) United States Patent
De Gier et al.

(10) Patent No.: US 9,079,182 B2
(45) Date of Patent: Jul. 14, 2015

(54) PROTECTION OF BIOANALYTICAL SAMPLE CHAMBERS

(75) Inventors: Ronald De Gier, Eindhoven (NL); Jozef C. M. Versleegers, Eindhoven (NL)

(73) Assignee: Biocartis NV, Mechelen (BE)

( * ) Notice: Subject to any disclaimer, the term of this patent is extended or adjusted under 35 U.S.C. 154(b) by 111 days.

(21) Appl. No.: 13/273,533

(22) Filed: Oct. 14, 2011

(65) Prior Publication Data

US 2012/0034687 A1 Feb. 9, 2012

Related U.S. Application Data

(63) Continuation of application No. PCT/CH2010/000095, filed on Apr. 9, 2010.

(30) Foreign Application Priority Data

Apr. 15, 2009 (EP) .................................... 09157972

(51) Int. Cl.

*C12M 1/34* (2006.01)
*C12M 3/00* (2006.01)
*B01L 9/00* (2006.01)
*B01L 7/00* (2006.01)

(52) U.S. Cl.

CPC ... *B01L 9/52* (2013.01); *B01L 7/52* (2013.01); *B01L 2200/141* (2013.01); *B01L 2200/18* (2013.01); *B01L 2300/041* (2013.01)

(58) Field of Classification Search

CPC . B01L 9/52; B01L 2200/18; B01L 2200/141; B01L 2300/041; B01L 2300/0636; B01L 7/52; B01J 2219/00722; B01J 2219/00659; C40B 40/06

USPC .......... 435/63, 287.2, 6.1; 422/401, 402, 417, 422/502, 503

See application file for complete search history.

(56) References Cited

U.S. PATENT DOCUMENTS 3,607,134 A 9/1971 McIntyre
3,633,877 A 1/1972 Bodine
4,256,697 A 3/1981 Baldwin (Continued)

FOREIGN PATENT DOCUMENTS

CH 667599 A5 10/1988
DE 19820466 A1 11/1999

(Continued)

OTHER PUBLICATIONS

Machine Translation of JP10096725 A.*

(Continued)

*Primary Examiner* — Michael Hobbs
(74) *Attorney, Agent, or Firm* — Kusner & Jaffe

(57) ABSTRACT

An apparatus for performing bioanalytic processing and analysis, a bioanalytical reaction device, and a cartridge thereof are provided. The cartridge contains a housing and at least one sample chamber in a platform for storing biological samples, which the bioanalytical reaction device can process and analyze. The platform is movably connected to the housing such that the platform is movable between a stowed position, in which the sample chamber is protected by the housing, and an extended position, in which the sample chamber is outside of the housing. The bioanalytical reaction device includes an actuation device for moving the platform between the stowed and extended positions.

29 Claims, 2 Drawing Sheets

(56) References Cited

U.S. PATENT DOCUMENTS

| | | | |
|---|---|---|---|
| 4,371,498 A | 2/1983 | Scordato et al. | |
| 4,571,087 A | 2/1986 | Ranney | |
| 4,849,340 A | 7/1989 | Oberhardt | |
| 4,857,274 A | 8/1989 | Simon | |
| 4,857,453 A | 8/1989 | Ullman et al. | |
| 4,874,137 A | 10/1989 | Chiba | |
| 4,943,522 A | 7/1990 | Eisinger et al. | |
| 4,965,047 A | 10/1990 | Hammond | |
| 4,983,523 A | 1/1991 | Li et al. | |
| 5,004,583 A | 4/1991 | Guruswamy et al. | |
| 5,096,669 A * | 3/1992 | Lauks et al. | 204/403.02 |
| 5,133,937 A | 7/1992 | Frackleton et al. | |
| 5,147,609 A | 9/1992 | Grenner | |
| 5,219,526 A | 6/1993 | Long | |
| 5,229,580 A | 7/1993 | Chioniere | |
| 5,296,374 A | 3/1994 | Culshaw et al. | |
| 5,397,537 A | 3/1995 | Kanda et al. | |
| 5,500,187 A | 3/1996 | Deoms et al. | |
| 5,504,007 A | 4/1996 | Haynes | |
| 5,504,013 A | 4/1996 | Senior | |
| 5,512,159 A | 4/1996 | Yoshioka et al. | |
| 5,578,495 A | 11/1996 | Wilks | |
| 5,589,136 A | 12/1996 | Northrup et al. | |
| 5,597,532 A | 1/1997 | Connolly | |
| 5,609,822 A | 3/1997 | Carey et al. | |
| 5,609,823 A | 3/1997 | Harttig et al. | |
| 5,622,871 A | 4/1997 | May et al. | |
| 5,627,041 A | 5/1997 | Shartle | |
| 5,726,026 A | 3/1998 | Wilding et al. | |
| 5,746,978 A | 5/1998 | Bienhaus et al. | |
| 5,770,029 A | 6/1998 | Nelson et al. | |
| 5,788,928 A | 8/1998 | Carey et al. | |
| 5,843,680 A | 12/1998 | Manian et al. | |
| 5,846,487 A | 12/1998 | Bennett, II | |
| 5,856,174 A | 1/1999 | Lipshutz et al. | |
| 5,882,903 A | 3/1999 | Andrevski et al. | |
| 5,912,134 A | 6/1999 | Shartle | |
| 5,928,880 A | 7/1999 | Wilding et al. | |
| 5,928,907 A | 7/1999 | Woudenberg et al. | |
| 5,945,334 A | 8/1999 | Besemer et al. | |
| 5,994,056 A | 11/1999 | Higuchi | |
| 6,077,669 A | 6/2000 | Little et al. | |
| 6,100,084 A | 8/2000 | Miles et al. | |
| 6,143,573 A | 11/2000 | Rao et al. | |
| 6,210,881 B1 | 4/2001 | Little et al. | |
| 6,329,139 B1 | 12/2001 | Nova et al. | |
| 6,369,893 B1 | 4/2002 | Christel et al. | |
| 6,391,541 B1 | 5/2002 | Petersen et al. | |
| 6,426,225 B1 | 7/2002 | Lewis et al. | |
| 6,431,476 B1 | 8/2002 | Taylor et al. | |
| 6,440,725 B1 | 8/2002 | Pourahmadi et al. | |
| 6,521,181 B1 | 2/2003 | Northrup et al. | |
| 6,524,532 B1 | 2/2003 | Northrup | |
| 6,551,817 B2 | 4/2003 | Besemer et al. | |
| 6,565,815 B1 | 5/2003 | Chang et al. | |
| 6,664,104 B2 | 12/2003 | Pourahmadi et al. | |
| 6,699,711 B1 | 3/2004 | Hahn et al. | |
| 6,713,297 B2 | 3/2004 | McMillan et al. | |
| 6,783,736 B1 | 8/2004 | Taylor et al. | |
| 6,818,185 B1 | 11/2004 | Petersen et al. | |
| 6,878,540 B2 | 4/2005 | Pourahmadi et al. | |
| 6,881,541 B2 | 4/2005 | Petersen et al. | |
| 6,887,693 B2 | 5/2005 | McMillan et al. | |
| 6,893,879 B2 | 5/2005 | Petersen et al. | |
| 6,987,018 B2 | 1/2006 | Taylor et al. | |
| 7,188,001 B2 | 3/2007 | Young et al. | |
| 7,569,346 B2 | 8/2009 | Petersen et al. | |
| 2002/0019060 A1 | 2/2002 | Petersen et al. | |
| 2002/0084329 A1 | 7/2002 | Kaye et al. | |
| 2004/0200909 A1 | 10/2004 | McMillan et al. | |
| 2005/0042137 A1 | 2/2005 | Petersen et al. | |
| 2005/0204373 A1 * | 9/2005 | Ueno et al. | 720/616 |
| 2005/0221281 A1 * | 10/2005 | Ho | 435/4 |
| 2006/0019379 A1 | 1/2006 | Taylor et al. | |
| 2006/0027686 A1 | 2/2006 | Taylor et al. | |
| 2006/0030038 A1 | 2/2006 | Taylor et al. | |
| 2008/0057572 A1 | 3/2008 | Petersen et al. | |
| 2010/0068706 A1 | 3/2010 | Pourahmadi et al. | |

FOREIGN PATENT DOCUMENTS

| | | | | |
|---|---|---|---|---|
| EP | 0271448 | A2 | 6/1988 | |
| EP | 0337690 | A1 | 10/1989 | |
| EP | 0512334 | A2 | 11/1992 | |
| EP | 0757830 | B1 | 12/1998 | |
| EP | 0706649 | B1 | 1/2001 | |
| EP | 1383602 | B1 | 6/2006 | |
| EP | 1181098 | B1 | 7/2006 | |
| EP | 0915173 | B1 | 1/2007 | |
| EP | 1179585 | B1 | 7/2008 | |
| GB | 938163 | A2 | 10/1963 | |
| JP | 10-96725 | A | 4/1998 | |
| JP | 2005-181143 | | 7/2005 | G01N 1/00 |
| JP | 2008-145125 | | 6/2008 | G01N 35/08 |
| WO | 9511454 | A1 | 4/1995 | |
| WO | 9529473 | A1 | 11/1995 | |
| WO | 9838487 | A2 | 9/1998 | |
| WO | 9958637 | A2 | 11/1999 | |
| WO | 2006136990 | A2 | 12/2006 | |
| WO | WO 2009/019448 | | 2/2009 | G01N 35/10 |
| WO | 2010064160 | A1 | 6/2010 | |

OTHER PUBLICATIONS

International Search Report dated Jun. 23, 2010 from PCT/CH2010/000095.

* cited by examiner

PROTECTION OF BIOANALYTICAL SAMPLE CHAMBERS

CROSS REFERENCE TO RELATED APPLICATIONS

This application is a continuation of International Application Ser. No. PCT/CH2010/000095 filed Apr. 9, 2010, now pending, which claims the benefit under 35 U.S.C. §119(a) of European Patent Application No. EP09157972, filed Apr. 15, 2009, the entire contents of both of which are incorporated herein by reference.

BACKGROUND OF THE INVENTION

1. Field of the Invention

This invention relates to apparatus for performing bioanalytic processing and analysis. In particular, the present invention relates to a bioanalytical reaction device and a cartridge thereof. The cartridge contains at least one sample chamber for storing biological samples, the bioanalytical reaction device can process and analyze.

2. Description of Related Art

One example of a bioanalytical reaction is the DNA polymerase chain reaction. The polymerase chain reaction (PCR) is a technique that permits amplification and detection of nucleic acid sequences. This technique has a wide variety of applications including DNA sequence analysis, detection of genetic mutations, diagnoses of viral infections, to name but a few. With the PCR a specific target sequence or strand of DNA can exponentially amplificated. The polymerase chain reaction comprises repeated cycles of target denaturation by heating the sample, primer annealing at a lower temperature and polymerase-mediated extension at a slight higher temperature. At the last step, the DNA polymerase synthesizes a new DNA strand complementary to the DNA template strand. Under optimal conditions, the amount of DNA target strands is doubled.

Besides to PCR, other bioanalytical reactions are known, for example the ligase chain reaction. More generally, several import bioanalytical methods are dependent upon changing the temperature of samples in a controlled fashion. Therefore, there is a need for the automation of these methods.

Several mechanical and automated bioanalytical reaction devices are known in the art. Certain devices use cartridges for storing biological samples, so that the one or more biological samples in one cartridge can be temporarily stored, while the biological samples in another cartridge can be processed in the bioanalytical reaction device. An operator only needs to remove the one cartridge from the device and insert the other cartridge into the device.

Such cartridges have various interfaces, such as one or more interfaces for heating a sample in the cartridge as well as one or more interfaces for optical reading out the result of the reaction, which is, for example, indicated by a certain color of the sample or by certain illuminating substances.

More specifically, the samples to be processed are stored in one or more chambers in the cartridge. In general, an interface is provided by a wall of one of the chambers through which the sample can be heated or analyzed. If an optical readout has to be performed, the chamber needs a transparent wall as interface.

SUMMARY OF THE INVENTION

It may be a problem, that such interfaces can be damaged or become dirty. Especially, when an operator handles such a cartridge, there is the possibility that he touches the cartridge at a location of an interface. An interface in the form of a thin wall can already be damaged by the force applied by a finger. Also, sweat or grease can be deposited on the interface in this way. A damaged or dirty interface can result in leakage from the cartridge or falsification of the optical detection.

It is an object of the invention to provide a safe and simple cartridge.

According to an exemplary embodiment of the invention, a cartridge for a bioanalytical reaction device is provided, the cartridge comprising at least one sample chamber for a sample, the at least one sample chamber having a wall through which the sample can be processed or analyzed by the bioanalytical reaction device, wherein the cartridge comprises a housing and a platform, the platform comprising the at least one sample chamber, wherein the platform is movably connected to the housing, such that the platform is movable between a stowed position, in which the wall is protected by the housing, and an extended position, in which the wall is outside of the housing.

Such a cartridge is protected from becoming damaged or polluted without unnecessarily complicating the structural design of the cartridge and the bioanalytical reaction device.

It is to be understood that herein the term "cartridge" is used for every kind of device capable of being connected with a bioanalytical reaction device. For example, a cartridge may be a holder, magazine, cassette or carrier.

The at least one sample chamber is placed on a platform (or disc or carrier) that can be extended from the cartridge. In the stowed position, the sample chamber is inside the housing of the cartridge. Consequently, the chamber is protected from getting damaged or dirty. For use, the platform is extended from the cartridge, e. g. for enabling it to interface with heaters and optical sensors of a bioanalytical reaction device.

The wall of the at least one sample camber can be a heating interface or, if the wall is translucent (at least for some wavelength), an optical interface for interfacing with components of the bioanalytical reaction device, such as a heater or an optical sensor.

According to a further exemplary embodiment, a cartridge is provided, wherein the at least one sample chamber is connected to a channel for filling the at least one sample chamber, the channel ending in the vicinity of the actuation means.

Vicinity may be understood as relating to a length of one of the following intervals: 0 to 15 millimeters (mm), 0 to 10 mm, and 0 to 5 mm.

The at least one sample chamber is connected to a channel for filling and draining the at least one sample chamber with fluids, such as the solution in which the sample is dissolved. Instead of a channel, every means adapted to conduct a fluid from one point to another, such as a line, a pipe or a hose, can be used. One end of the channel can be connected to a line of the bioanalytical reaction device, which can pump fluids over the line into the sample chamber. The end of the channel is part a fluidal interface of the cartridge.

Placing the end of the channel in the vicinity of the actuation means has the advantage that a mechanical connection for moving the platform and a fluidal connection can be integrated in one component of the cartridge.

According to a further exemplary embodiment, a cartridge is provided, wherein a part of the channel is located within the actuation means. The channel may be located in a shaft for rotating the platform or in a spindle for moving the platform. This is one possibility of integrating the mechanical and the fluidal connection of the cartridge. Further the at least one sample chamber may be filled independent of the position of the platform.

According to a further exemplary embodiment, a cartridge is provided, wherein the wall is arranged at a first side of the platform, wherein the platform has a second side opposite to the first side, and wherein the platform in the extended position is accessible from the first side and the second side by the bioanalytical reaction device for processing or analyzing the sample. The sample within the at least sample chamber may be processed or analyzed simultaneously from two sides of the platform.

According to a further exemplary embodiment, a cartridge is provided, wherein at least one dimension of the cartridge with the platform in the extended position is bigger than this dimension of the cartridge with the platform in the stowed position. Therefore, the cartridge with the platform in the stowed position can easily be stored.

According to a further exemplary embodiment, a cartridge is provided, wherein the platform is rotatably connected to the housing. Preferably, the actuation means is a shaft and the platform is connected to the shaft for rotating the platform about a rotation axis. More preferably, the shaft extends up to an opening in the housing. In this way, the mechanical connection of an actuator of the bioanalytical reaction device to the cartridge for rotating the platform can easily be established. Further, the opening in the housing may provide a guidance for the shaft, and therefore for the platform.

Alternatively, according to a further exemplary embodiment, a cartridge is provided, wherein the platform is slidably connected to the housing. The actuation means may be a spindle for translatorily moving the platform from the stowed position to the extended position.

According to a further exemplary embodiment, a cartridge is provided, wherein the platform has the form of a plate, which, in the stowed position, is arranged between a first wall and a second wall of the housing. A platform in the form of a plate, i. e. a component with one dimension much smaller than the two other dimensions in different directions, can be provided with more than one sample chamber and all of the sample chambers are easily accessible by a bioanalytical reaction device.

According to a further exemplary embodiment, a cartridge is provided, wherein the wall of the at least one sample chamber is thin. For minimizing the thermal barrier, the wall may be thin and can for example be a foil with a high heat conductance. Herein, with a thin wall a wall is meant which has a thickness of about less than 200 micrometers (μm). A thin wall may also optimize the transparence of the optical interface of the at least one sample chamber.

According to a further exemplary embodiment, a cartridge is provided, wherein the at least one sample chamber is formed by an opening in the platform which is covered by a foil or thin layer forming the thin wall.

Another aspect of the invention is a bioanalytical reaction device having a slot or receptacle for receiving the cartridge, comprising an actuator for extending and stowing the platform of the cartridge. The actuator may be a step motor.

According to a further exemplary embodiment, a bioanalytical reaction device is provided, having a reservoir for filling the at least one sample chamber, wherein the reservoir is connectable with the at least one sample chamber over a line ending in a mechanical connection of the actuator with the actuation means for moving the platform. Within the mechanical connection, there also may be the fluidal connection of the bioanalytical reaction device with the cartridge. The fluidal interface or fluidal connection of the bioanalytical reaction device and the mechanical connection are integrated in one component.

According to a further exemplary embodiment, a bioanalytical reaction device is provided having a cartridge presence sensor for detecting the presence and/or the correct insertion of the cartridge in the slot. Only when a cartridge is present in the slot, the bioanalytical reaction device should operate the line for filling the sample chamber. Otherwise, fluids can polute the interior of the bioanalytical reaction device.

According to a further exemplary embodiment, a bioanalytical reaction device is provided, which is adapted to effect the actuator to move the platform in the extended position, when the cartridge presence sensor detects the presence of the cartridge in the slot.

These and other aspects of the invention will be apparent from and elucidated with reference to the embodiment described hereinafter.

BRIEF DESCRIPTION OF THE DRAWINGS

Below, an embodiment of the present invention is described in more detail with reference to the attached drawings. It shows.

DETAILED DESCRIPTION OF EMBODIMENTS

Figure 1:
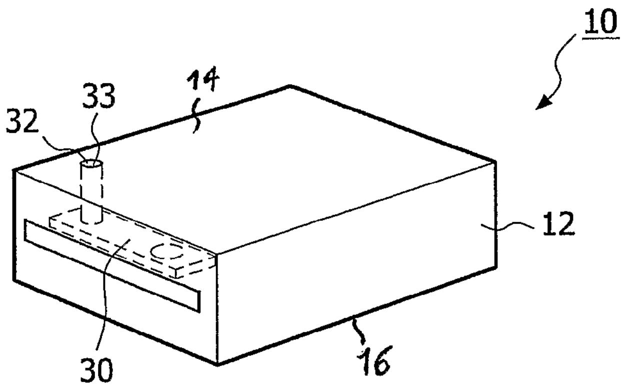
FIG. 1 shows a perspective view of a cartridge for a bioanalytical reaction device with a platform in the stowed position.

FIG. 1 shows a perspective view of a cartridge 10 for a bioanalytical reaction device. The cartridge 10 has a housing 12 with an upper cover or wall 14 and a lower cover or wall 16. It is to be understood that the wording “upper” and “lower” are used for reasons of simplicity and are not intended to be limiting. For example, the cartridge 10 may be inserted into a bioanalytical reaction device not in the shown orientation but in an upstanding orientation.

FIG. 1 shows the platform 30 in a stowed position. The platform 30 is rotatably connected with the housing 12 via a shaft 32 as actuation means. The shaft 32 is guided by the opening 33 in the upper cover 14. By rotating the shaft 32 about the rotation axis A the platform 30 can be extended from the housing 12 of the cartridge 10.

Figure 2:
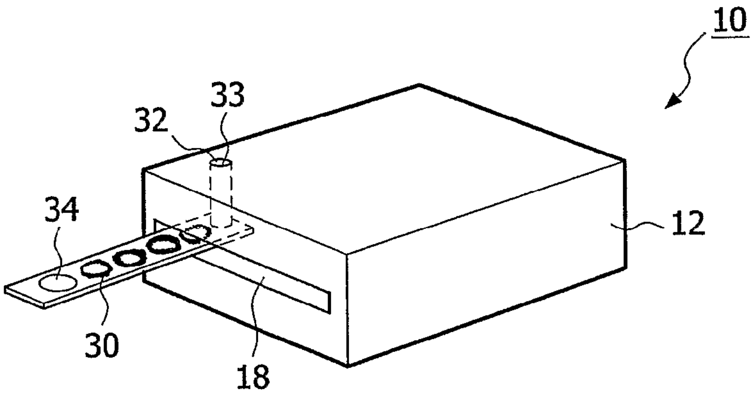
FIG. 2 shows a perspective view of the cartridge of FIG. 1 with the platform in an extended position.

FIG. 2 shows a perspective view of the cartridge 10 with the platform 30 in an extended position. The platform 30 has exited the housing 12 through a slit 18 in the housing 12 between the upper cover 14 and the lower cover 16. By a further rotation of the shaft 32 in the opposite direction around the rotation axis A, the platform 30 can again be stowed in the housing 12. In the stowed position the platform 30 is protected from being damaged or getting dirty. In the extended position the platform 30 can be accessed by actuators like a heater or a sensor of a bioanalytical reaction device.

Further, in FIG. 2 it can be seen that the platform 30 comprises five sample chambers 34.

Figure 3:
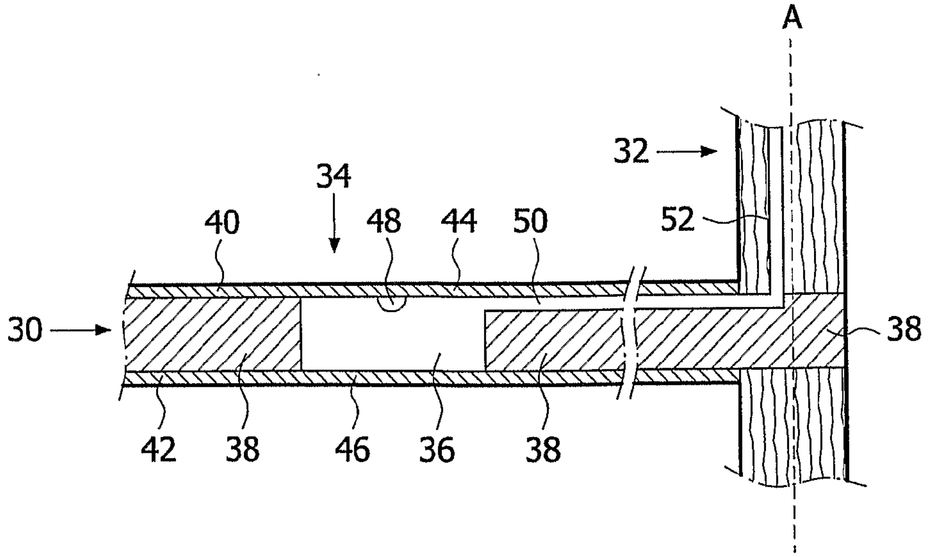
FIG. 3 shows a schematic cross sectional view of parts of the platform of FIG. 2.

FIG. 3 shows a schematic cross-sectional view of parts of the platform 30. In particular, the left-hand side of the drawing shows a cross-sectional view of a sample chamber 34, the right-hand side of the drawing shows a cross-sectional view of the vicinity of the rotation axis A.

Platform 30 comprises a plate 38 that may be made of plastics. For each sample chamber 34 there is an opening 36 in the plate 38. On one first side of the plate 38, a first or upper foil 40 is applied. For example, the upper foil 40 may be glued to the plate 38. In the shown embodiment, the upper foil 40 has a thickness of about 100 μm. In the region of the opening 36 the upper foil 40 forms a thin wall of the sample chamber, the thin wall being a heating interface 44 of the sample chamber 34. If a heating or cooling source is arranged outside of the sample chamber 34 in the region of the heating interface 44 heat may be transferred to the interior of the sample chamber 34 or may exit it.

On the other second side of the plate 38, opposite to the first side, there is applied a second or lower foil 42 of a translucent material. The lower foil 42 may be glued or in some other way be connected to the plate 38. Also, the lower foil 42 has a thickness of about 100 μm. In the region of the opening 36, the lower foil 42 forms an optical interface 46 of the sample chamber 34. In this region, light can penetrate the translucent lower foil 42. Light coming from the interior of the sample chamber can be detected by an optical sensor arranged near the optical interface 46 of the sample chamber 34.

Further, FIG. 3 shows a first channel 48 formed by a groove or notch in the surface of the plate 38 and covered by the upper foil 40. In the same way a second channel 50 is formed connecting the sample chamber 34 with a third channel 52 within the shaft 32.

It is to be understood, that there are other possibilities to form the sample chamber 34 and the channels 48, 50, 52 within the platform 30. For example, the platform 30 may be manufactured from two parts being mirror symmetric and having openings and grooves which form the sample chambers and the channels, when the two parts are connected with each other. Further, it would be possible, to provide the plate 30 with pits. With a foil or thin layer covering the pits sample chambers can be formed on the plate. In this case, such sample chambers would have only one interface.

Figure 4:
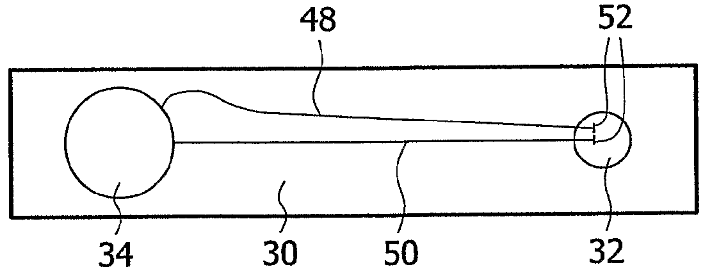
FIG. 4 is a schematic topview on the platform of FIG. 2.

From FIG. 4 being a schematic top view on the platform 30, it can be seen, that the sample chambers 34 are fluidly connected via channels 48, 50 with channels 52 formed in the shaft 32 in the vicinity of the rotation axis A. Over the channels 48 and 50 each sample chamber 34 can be filled with solutions, e.g. a solution containing DNA fragments to be analyzed or amplified. Also, the sample chambers 34 can be emptied by conducting a gas, e.g. air, or other solutions or liquids like water through the channels 48, 50 into the sample chamber 34.

The shaft 32 with the channels 52 is a fluidal interface 54 of the platform 30.

Since the fluidal interface 54 is in the vicinity of the rotation axis A, it can be accessed over the mechanical connection of the bioanalytical reaction device for rotating the platform 30. Therefore, the mechanical connection and the fluidic connection are combined and the number of connections between the cartridge 10 and a bioanalytical reaction device is reduced.

Figure 5:
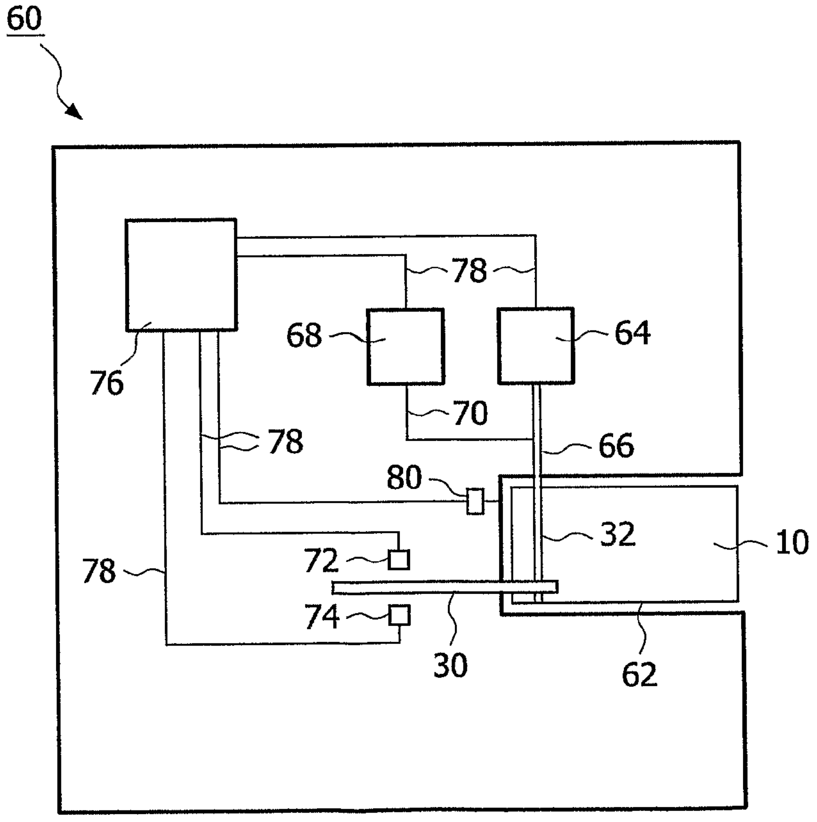
FIG. 5 shows a schematical diagram of functional components of a bioanalytical reaction device.

FIG. 5 shows a schematical diagram of a bioanalytical reaction device 60. The bioanalytical reaction device 60 has a slot 62 for receiving the cartridge 10. With an actuator 64, for example a step motor, which is rotatably connected with the shaft 32 the platform 30 can be extended from the cartridge 10 to an extended position and be returned in a stowed position. FIG. 5 shows the platform 30 in an extended position. The fluid lines 70 are connected with inlets and outlets combined with the mechanical connection 66. The inlets and outlets fit to their respective counterparts formed in the shaft 32. A pump and reservoir mechanism 68 can fill the sample chambers 34 in the platform 30. The bioanalytical reaction device has one or more heaters 72 for heating the samples within the sample chambers 34 from the first side of the platform 30 and one or more optical sensors 74 for analyzing the light emitted from the interior of the sample chambers 34 from the second side of the platform 30.

Over a controller 76 which is connected over control lines 78 with the actuator 64, the pump and reservoir mechanism 68, the heater 72 and the optical sensor 74, the bioanalytical reaction device 60 can control the analysis and processing of the samples in the sample chambers in an automated way. For example, the bioanalytical reaction device 60 can conduct the above mentioned PCR procedure.

Further, it is possible, that the bioanalytical reaction device 60 controls the extension and the stowing of the platform 30 in an automated way. When an operator inserts the cartridge 10 into the slot 62, a mechanical sensor 80 detects the presence of the cartridge 10. Alternatively, the detection can be done with an optical sensor. With this input the controller 76 directs the actuator 64 to rotate the platform 30 in the extended position. After that, several processings, like filling the chambers with different solutions, heating the sample chambers 34 and analyzing the light from the sample chambers 34, can be performed by the controller 76. When the processing and the analysis is done, the controller 76 directs the actuator 64 to rotate the platform 30 back to the stowed position and an operator can remove the cartridge 10 from the bioanalytical reaction device 60.

While the invention has been illustrated and described in detail in the drawings and foregoing description, such illustration and description are to be considered illustrative or exemplary and not restrictive; the invention is not limited to the disclosed embodiment. Other variations to the disclosed embodiment can be understood and effected by those skilled in the art and practising the claimed invention, from a study of the drawings, the disclosure, and the appended claims. In the claims, the word "comprising" does not exclude other elements or steps, and the indefinite article "a" or "an" does not exclude a plurality. A single processor or controller or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

What is claimed is:

1. A cartridge for a bioanalytical reaction device, said cartridge comprising:

a housing;

a platform having one or more sample chambers provided therein for receiving a respective sample, each said sample chamber is defined by an opening in the platform, wherein at least one of the sample chambers includes a wall that allows the sample to be processed or analyzed by the bioanalytical reaction device through the wall, wherein the platform is moveably connected to the housing for movement of the platform relative to the housing, said platform moveable between (i) a stowed position, in which the wall is protected by the housing so that the sample cannot be processed or analyzed by the bioanalytical reaction device through the wall, and (ii) an extended position, in which the wall is outside of the housing for processing or analyzing the sample with the bioanalytical reaction device through the wall; and an actuation device connected to the platform to move the platform between the stowed and the extended positions.

2. The cartridge of claim 1, wherein the at least one sample chamber is connected to a channel for filling the at least one sample chamber, the channel ending in the vicinity of the actuation device.

3. The cartridge of claim 2, wherein a part of the channel is located within the actuation device.

4. The cartridge of claim 1, wherein the wall is arranged at a first side of the platform, the platform having a second side opposite to the first side, and wherein the platform, when in the extended position, is accessible from the first side and the second side by the bioanalytical reaction device for processing or analyzing the sample.

5. The cartridge of claim 1, wherein at least one dimension of the cartridge with the platform in the extended position is bigger than the dimension with the platform in the stowed position.

6. The cartridge of claim 1, wherein the platform is rotatably connected to the housing.

7. The cartridge of claim 6, wherein the actuation device is a shaft and the platform is connected to the shaft for rotating the platform about a rotation axis.

8. The cartridge of claim 1, wherein the platform is slidably connected to the housing.

9. The cartridge of claim 1, wherein the platform comprises a plate having said opening formed therein, said plate arranged between a first wall of the housing and a second wall of the housing, in the stowed position.

10. The cartridge of claim 1, wherein the wall is formed by a foil that covers the opening.

11. A bioanalytical reaction device, comprising:
 a cartridge having:
  a housing,
  a platform having one or more sample chambers provided therein for receiving a respective sample, each said sample chamber is defined by an opening in the platform, wherein at least one of the sample chambers includes a wall that allows the sample to be processed or analyzed through the wall,
  wherein the platform is moveably connected to the housing for movement of the platform relative to the housing, said platform moveable between (i) a stowed position, in which the wall is protected by the housing so that the sample cannot be processed or analyzed through the wall, and (ii) an extended position, in which the wall is outside of the housing for processing or analyzing the sample through the wall, and
  an actuation device connected to the platform to move the platform between the stowed and the extended positions;
 a slot for receiving the cartridge; and
 an actuator for engaging the actuation device when the cartridge is received in the slot to move the platform between the stowed and the extended positions.

12. The bioanalytical reaction device of claim 11, wherein the actuator is a motor.

13. The bioanalytical reaction device of claim 11, wherein the cartridge further comprises:
 a reservoir for filling the at least one sample chamber, wherein the reservoir is connectable, by the actuator, with the at least one sample chamber over a line extending through the actuator.

14. The bioanalytical reaction device of claim 11, further comprising a cartridge presence sensor for detecting a presence of the cartridge in the slot.

15. The bioanalytical reaction device of claim 14, wherein the actuator engages the actuation device to move the platform to the extended position when the cartridge presence sensor detects the presence of the cartridge in the slot.

16. The bioanalytical reaction device of claim 11, wherein the platform is rotatably connected to the housing.

17. The bioanalytical reaction device of claim 11, wherein the actuation device is a shaft and the platform is connected to the shaft for rotating the platform about a rotation axis.

18. The bioanalytical reaction device of claim 11, wherein the platform is slidably connected to the housing.

19. The bioanalytical reaction device of claim 11, wherein the platform comprises a plate having said opening formed therein, said plate arranged between a first wall of the housing and a second wall of the housing, in the stowed position.

20. The bioanalytical reaction device of claim 11, wherein the wall is formed by a foil that covers the opening.

21. A cartridge for a bioanalytical reaction device, comprising:
 a housing adapted to be received in the bioanalytical reaction device;
 a platform having one or more sample chambers provided therein for receiving a respective sample, each sample chamber defined by an opening in the platform, wherein at least one of the sample chambers includes a wall that allows the sample to be processed or analyzed by the bioanalytical reaction device through the wall, wherein the platform is moveably connected to the housing such that, when the housing is received in the bioanalytical reaction device, the platform is moveable between (i) a stowed position, in which the wall is inside the housing, and (ii) an extended position, in which the wall is outside of the housing, the sample of the at least one sample chamber is processed or analyzed by the bioanalytical reaction device through the wall when the platform is in the extended position; and
 a shaft rotatably connecting the platform to the housing for movement of the platform between the stowed and the extended positions.

22. The cartridge of claim 21, further comprising a fluid channel defined in the shaft, the fluid channel being in fluid communication with the at least one sample chamber.

23. The cartridge of claim 21, wherein said wall is formed by a foil that covers the opening.

24. The cartridge of claim 1, wherein said wall provides an interface for heating or cooling the at least one sample chamber.

25. The cartridge of claim 1, wherein said wall provides an optical interface allowing light to travel to and from the at least one sample chamber.

26. The cartridge of claim 1, wherein said wall is arranged at a first side of the platform, and said at least one sample chamber has a second wall at a second side of the platform opposite to the first side of the platform.

27. The cartridge of claim 1, wherein said wall provides at least one of:
 (i) an interface that allows the transfer of heat therethrough, and
 (ii) an optical interface that allows light to penetrate therethrough.

28. The bioanalytical reaction device of claim 11, wherein said wall of the cartridge provides at least one of:
 (i) an interface that allows the transfer of heat therethrough, and
 (ii) an optical interface that allows light to penetrate therethrough.

29. The cartridge of claim 21, wherein said wall provides at least one of:

(i) an interface that allows the transfer of heat therethrough, and (ii) an optical interface that allows light to penetrate therethrough.

* * * * *